(12) United States Patent
Lee

(10) Patent No.: US 6,367,477 B2
(45) Date of Patent: Apr. 9, 2002

(54) MULTI-COLORED CONTRACEPTIVE SHEATH

(76) Inventor: Calvin S. Lee, 2835 Sierra Grande St., Pasadena, CA (US) 91107-3448

( * ) Notice: Subject to any disclaimer, the term of this patent is extended or adjusted under 35 U.S.C. 154(b) by 0 days.

(21) Appl. No.: 09/776,151

(22) Filed: Feb. 5, 2001

Related U.S. Application Data

(63) Continuation-in-part of application No. 09/617,684, filed on Jul. 17, 2000, now abandoned.

(51) Int. Cl.⁷ .................................................. A61F 6/04
(52) U.S. Cl. ........................ 128/842; 128/844; 128/918
(58) Field of Search ................................ 128/842, 844, 128/918; 604/347–353

(56) References Cited

U.S. PATENT DOCUMENTS

| | | | | |
|---|---|---|---|---|
| 5,284,158 A | * | 2/1994 | Mallette | 128/918 |
| 5,284,159 A | * | 2/1994 | Wilk | 128/844 |
| 5,318,042 A | * | 6/1994 | Gray | 128/844 |
| 5,398,699 A | * | 3/1995 | Fuegus | 128/844 |
| 5,411,034 A | * | 5/1995 | Beck | 128/844 |
| 5,571,567 A | * | 11/1996 | Shah | 427/379 |

* cited by examiner

*Primary Examiner*—Michael A. Brown
(74) *Attorney, Agent, or Firm*—Erik M. Arnhem

(57) ABSTRACT

A contraceptive sheath can provide extra leak protection by forming at least one latex film over the bulbous closed end of a latex sheath liner. A transparent elastic covering overlies the sheath outer surface to seal the latex films against separation from the latex liner.

12 Claims, 2 Drawing Sheets

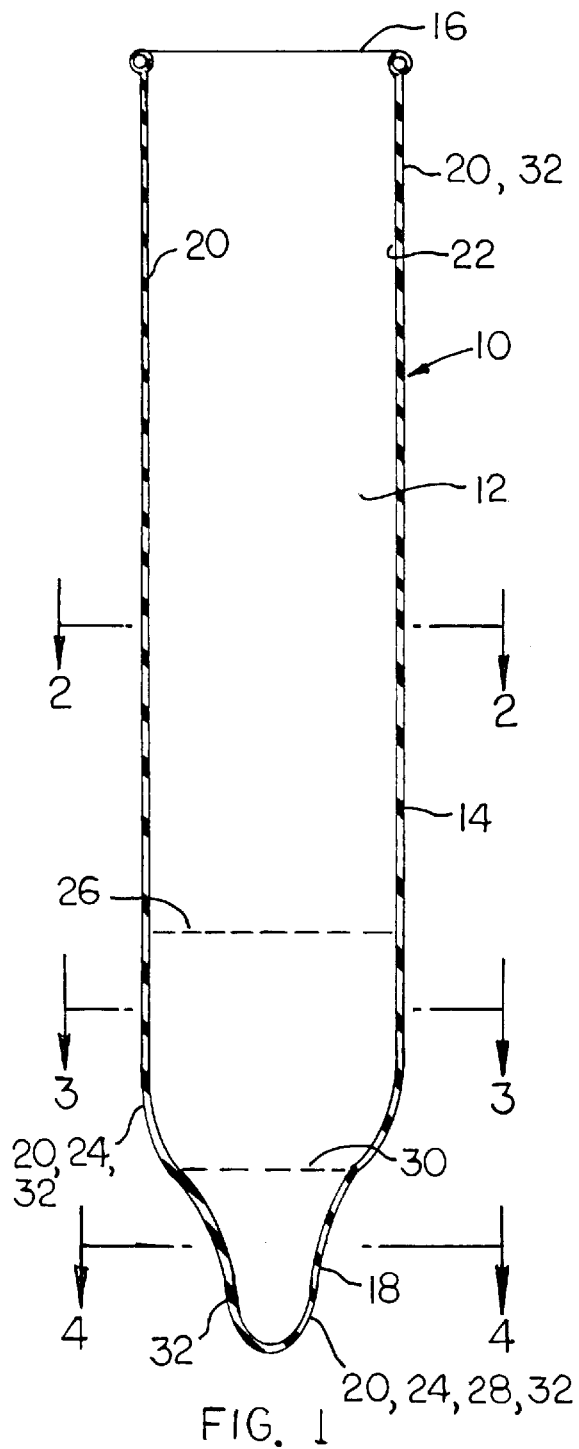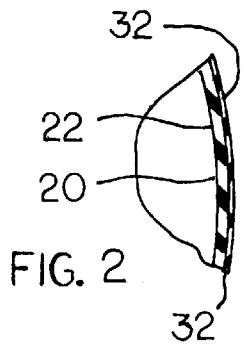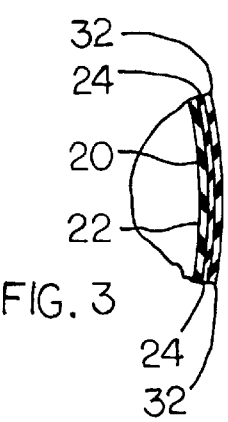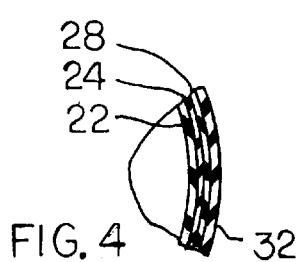

MULTI-COLORED CONTRACEPTIVE SHEATH

CROSS REFERENCE TO A RELATED PATENT APPLICATION

This is a continuation-in-part of my U.S. patent application Ser. No. 09/617,684 filed on Jul. 17, 2000, now abandoned.

FIELD OF THE INVENTION

This invention relates to contraceptive sheaths usable during sexual intercourse to prevent conception.

BACKGROUND OF THE INVENTION

Contraceptive sheaths have been devised for insertion over the male penis to prevent conception during sexual intercourse. Such contraceptive sheaths typically take the form of an elastic tubular sleeve having a bulbous closed end that traps the seminal fluid against escape from the sheath during sexual intercourse.

Typically the contraceptive sheath is formed by dipping a glass mold into a molten bath of latex material. The mold is removed from the bath, so that some of the latex adheres to the mold surface. After drying, the latex is peeled from the mold to form the finished product.

SUMMARY OF THE INVENTION

The present invention relates to a contraceptive sheath that has multiple films of latex material, including a latex tubular liner that defines the sheath interior surface, at least one latex film covering the bulbous end of the liner, and a third transparent film covering the entire outer surface of the liner and the latex film (or films). The transparent outer film acts as a sealer to prevent the latex films from peeling or separating from the latex liner.

In one embodiment of the invention there are two latex films between the liner and the transparent sealer film. In another embodiment of the invention there is a single latex film covering the bulbous end of the latex liner. The latex film (or films) strengthen the contraceptive sheath against rupture.

In preferred practice of the invention the liner and the strengthening latex films are formed of contrasting colors, e.g. a blue coloration for the liner, white coloration for the first film, and red coloration for the second film.

The contraceptive sheath of the invention can be formed by a process that involves dipping a glass mold into a latex bath to form the tubular liner, dipping the mold partway into a second latex bath to form the first latex film on the liner outer surface, dipping the mold into a third latex bath to form the second latex film, and dipping the mold into a fourth bath to form an outer transparent covering over the full length of the tubular sheath. The fourth bath is preferably a molten non-viscous plastic.

The dipping operations are performed in rapid sequence, so that the respective latex layers on the mold are only partially dry when the next dipping operation is carried out. Each latex film is bonded to the next film without adhesives or bonding agents.

The respective latex baths have different colorations, to achieve a contraceptive sheath having multiple colorations, e.g. red coloration on the bulbous end of the sheath, white coloration for a minor portion of the sheath tubular length, and blue coloration for a major portion of the sheath tube length.

The multi-layer sheath construction provides redundant protection against rupture or leakage, particularly at the bulbous closed end of the sheath. Also, the multiple coloring of the sheath gives the contraceptive device a distinctive appearance. The transparent film on the sheath outer surface seals the latex layers against peeling or separation from the one piece latex liner.

Further features of the invention will be apparent from the attached drawings and description of a contraceptive sheath embodying the invention.

BRIEF DESCRIPTION OF THE DRAWINGS

FIG. 1 is a longitudinal sectional view taken through a contraceptive sheath constructed according to the invention.

FIG. 2 is an enlarged fragmentary sectional view taken on line 2—2 in FIG. 1.

FIG. 3 is an enlarged fragmentary sectional view taken on line 3—3 in FIG. 1.

FIG. 4 is an enlarged fragmentary sectional view taken on line 4—4 in FIG. 1.

DESCRIPTION OF A PREFERRED EMBODIMENT OF THE INVENTION

Figure 5:
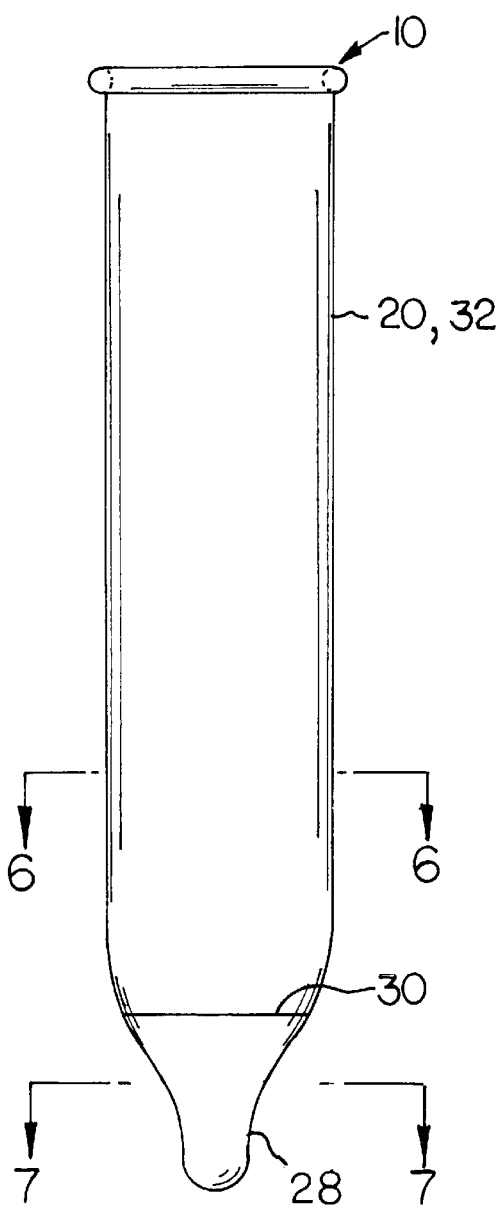
FIG. 5 is an elevational view of another contraceptive sheath embodying the invention.

Referring to FIG. 1, there is shown a contraceptive sheath 10 adapted to be placed over a male penis during sexual intercourse to trap seminal fluid from escaping out of the sheath interior space 12. The contraceptive sheath includes an elongated tubular section 14, an open end 16, and a closed bulbous end 18.

FIG. 1 shows the sheath as a single latex layer. However, the sheath actually has multiple latex layers, as shown in the fragmentary enlarged sectional views, i.e. FIGS. 2, 3 and 4. The inner surface 22 of the contraceptive sheath is formed by a latex liner 20 extending the full length of the sheath. Liner 20 is formed on a glass mold having a surface contour corresponding to inner surface 22 of the latex sheath.

The glass mold is dipped into a molten latex bath and drawn out of the bath to form the thin flexible latex liner 20.

A first latex film 24 is formed on the outer surface of liner 20 by dipping the mold into a second molten latex bath, preferably before the liner material has fully dried. Latex film 24 covers the bulbous lower end of liner 20 and part of the liner tubular section. In FIG. 1, dashed line 26 indicates the upper limit of latex film 24.

A second latex film 28, is formed on the outer surface of film 24, e.g. by dipping the mold in a third molten latex bath, preferably before the film 24 has completely dried, i.e. while the surface of film 24 is in a tacky condition. In FIG. 1, dashed line 30 indicates the upper limit of latex film 28.

An outer transparent elastic film 32 is formed on the outer surface of the contraceptive sheath, so as to cover the outer surface of liner 20, the outer surface of film 24, and the outer surface of film 28. Transparent film 32 extends the full length of the contraceptive sheath, to prevent films 24 and 28 from peeling or separating from liner 20. Elastic film 32 is formed by dipping the mold into a fourth bath of non-viscous molten transparent plastic or latex material while the surfaces of films 24 and 28 are still tacky.

The latex bath for liner 20 can have a blue coloration, the latex bath for film 24 can have a white coloration, and the latex bath for film 28 can have a red coloration. Transparent outer film 32 seals the films to liner 20.

The multi-layer sheath construction provided by films 24, 28 and 32, provides redundant protection against rupture or leakage. A multi-layer latex thickness is achieved at the bulbous closed end 18 of the sheath, where leak protection is especially necessary. The extra latex films 24 and 28 cover primarily the bulbous closed end of the sheath, so that the sheath wall has a desired flexibility and thinness along a major portion of the sheath length. The transparent outer film 32 is preferably very thin, so that it does not materially affect the flexibility of the contraceptive sheath.

Figure 6:
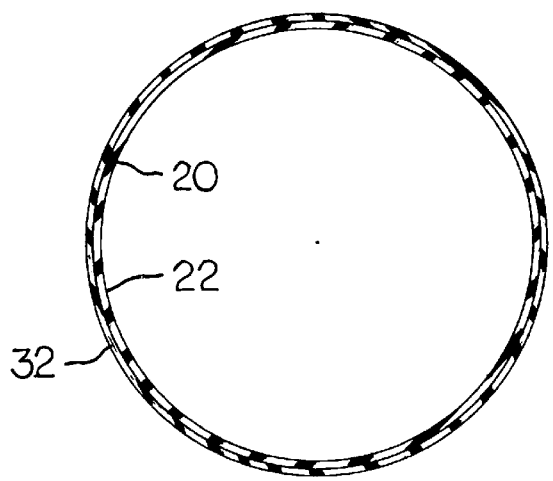
FIG. 6 is an enlarged sectional view taken on line 6—6 in FIG. 5.
Figure 7:
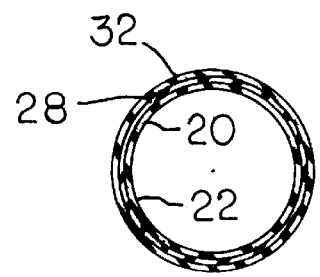
FIG. 7 is an enlarged sectional view taken on line 7—7 in FIG. 5.

FIGS. 5 through 7 show another form that the invention can take. The sheath construction of FIGS. 5 through 7 is the same as the construction depicted in FIGS. 1 through 4, except that elastic film 24 is omitted. Elastic film 28 is formed directly on the outer surface of elastic liner 20.

Liner 20 is formed on a glass mold having a surface contour corresponding to inner surface 22 of the latex sheath 10. Latex film 28 is formed on the outer surface of liner 20 by dipping the coated mold into a second molten latex bath, preferably before the liner material has fully dried. Latex film 28 covers the bulbous lower end of liner 20 to provide rupture protection for that portion of the sheath that is most likely to experience the greatest expansion (or wall thickness reduction). In FIG. 5 line 30 indicates the upper limit of latex film 28.

An outer transparent elastic film 32 is formed on the outer surface of liner 20 and latex film 28. Transparent film 32 extends the full length of the contraceptive sheath to prevent film 28 from peeling or separating from liner 20. Transparent film 32 is formed by dipping the coated mold into a third molten bath of non-viscous molten transparent material (preferably a plastic), while the outer surfaces of liner 20 and latex film 28 are still tacky.

As with the contraceptive sheath of FIGS. 1 through 4, liner 20 and latex film 28 have contrasting colorations, incorporating differently colored dyes into the first and second baths.

The multi-layer sheath construction of FIGS. 5 through 7 provides redundant protection against rupture, particularly at the bulbous closed end of the sheath. The transparent outer film 32 acts as a sealer to prevent latex film 28 from peeling away from liner 20. The multi-layer sheath is preferably formed without using extraneous adhesives between liner 20, latex film 28 and outer film 32.

What is claimed:

1. A contraceptive sheath for a male penis, comprising: an elastic sleeve that includes an elastic liner having an elongated tubular section, an open end, and a bulbous closed end; a first continuous elastic film on the bulbous end of the liner and a minor portion of the liner tubular section; a second continuous elastic film covering only the bulbous closed end of the liner; and a third outer transparent elastic film covering the entire outer surface of said liner, first film and second film.

2. The contraceptive sheath of claim 1, wherein said liner has a first coloration, said first film has a second coloration, and said second film has a third coloration.

3. The contraceptive sheath of claim 2, wherein said first, second and third elastic films are formed by dipping the elastic liner into separate baths of elastic materials.

4. The contraceptive sheath of claim 2, wherein said first and second films are latex.

5. The contraceptive sheath of claim 2, wherein said first, second and third elastic films are formed by dipping the elastic liner into separate baths of molten elastic materials while the liner surface is in a tacky condition.

6. A contraceptive sheath for a male penis, comprising: an elastic sleeve that includes an elastic liner having an elongated tubular section, an open end, and a bulbous closed end; a first continuous elastic film covering only the bulbous closed end of said liner; and a second outer transparent elastic film covering the entire outer surface of said liner and said first film.

7. The contraceptive sheath of claim 6, wherein said liner and said first film have different colorations.

8. The contraceptive sheath of claim 6, wherein said first and second films are formed by dipping the elastic liner into separate baths of molten elastic materials.

9. The contraceptive sheath of claim 6, wherein said liner and said elastic films are adherred directly together without extraneous adhesives.

10. A contraceptive sheath for a male penis, comprising: an elastic liner having an elongated tubular section, an open end, and a bulbous closed end; at least one continuous anti-rupture elastic film covering the bulbous closed end of said liner; and an outer transparent sealer film covering the entire surface of said liner and said anti-rupture film.

11. The contraceptive sheath of claim 10, wherein said liner and said anti-rupture film have different colorations.

12. The contraceptive sheath of claim 10, wherein said liner and said films are adherred directly together without extraneous adhesives.

* * * * *